United States Patent [19]
Clawson

[11] Patent Number: 5,989,187
[45] Date of Patent: Nov. 23, 1999

[54] METHOD AND SYSTEM FOR GIVING REMOTE EMERGENCY MEDICAL COUNSELING FOR CHILDBIRTH PATIENTS

[75] Inventor: Jeffrey J. Clawson, Salt Lake City, Utah

[73] Assignee: Medical Priority Consultants, Inc., Salt Lake City, Utah

[21] Appl. No.: 08/832,615

[22] Filed: Mar. 28, 1997

Related U.S. Application Data

[60] Provisional application No. 60/014,741, Mar. 29, 1996.

[51] Int. Cl.$^6$ ...................................................... A61B 5/00
[52] U.S. Cl. ........................................... 600/300; 128/903
[58] Field of Search ..................................... 128/903, 905, 128/920, 923, 924, 925; 600/300, 481; 606/119, 125, 126, 127, 122, 202; 364/224.5, 224.6, 274, 274.1, 274.9, 275

[56] References Cited

U.S. PATENT DOCUMENTS

| | | | |
|---|---|---|---|
| 4,130,881 | 12/1978 | Haessler et al. | 364/900 |
| 4,237,344 | 12/1980 | Moore | 179/2 A |
| 4,489,387 | 12/1984 | Lamb et al. | 364/514 |
| 4,839,822 | 6/1989 | Dormond et al. | 364/513 |
| 4,858,121 | 8/1989 | Barber et al. | 364/406 |
| 4,945,476 | 7/1990 | Bodick et al. | 364/413.02 |
| 5,063,522 | 11/1991 | Winters | 395/51 |
| 5,065,315 | 11/1991 | Garcia | 364/413.01 |
| 5,072,383 | 12/1991 | Brimm et al. | 364/413.02 |
| 5,253,164 | 10/1993 | Holloway et al. | 364/406 |
| 5,255,187 | 10/1993 | Sorensen | 364/413.02 |
| 5,438,996 | 8/1995 | Kemper et al. | 600/448 |
| 5,471,382 | 11/1995 | Tallman et al. | 364/406 |
| 5,596,994 | 1/1997 | Bro | 128/732 |
| 5,722,418 | 3/1998 | Bro | 128/905 |

*Primary Examiner*—Robert L. Nasser
*Attorney, Agent, or Firm*—Lloyd W. Sadler

[57] ABSTRACT

A method and system for providing emergency medical counseling to childbirth patients remotely is described. A consistent, standard and systematic process is provided which in combination with adequate training, supervision and quality assurance serves to provide a method for gathering emergency medical information regarding providing emergency medical dispatch services to childbirth patients, categorizing such information into various determinant levels for appropriate response, and for giving qualified emergency medical information to callers thereby permitting "zero time" response by those at the scene. By using this invention properly a dispatcher is guided through the interrogation of callers concerned with childbirth patients, gathering critical information and giving the appropriate guidance to the caller. This invention specifically guides the dispatcher through the steps of the procedure for giving remote emergency medical counsel to childbirth patients, thereby providing the "zero time" response by utilizing those at the scene of the emergency.

3 Claims, 5 Drawing Sheets

Microfiche Appendix Included
(1 Microfiche, 20 Pages)

METHOD AND SYSTEM FOR GIVING REMOTE EMERGENCY MEDICAL COUNSELING FOR CHILDBIRTH PATIENTS

This application is based on Provisional Application Ser. No. 60/014,741, which was filed on Mar. 29, 1996, and priority is claimed thereto.

BACKGROUND OF THE INVENTION

1. Field of the Invention

This invention relates to methods and systems for processing and responding to emergency medical inquiries. Specifically, this invention relates to the process of providing emergency medical counsel, instruction or advice to callers who are inquiring concerning childbirth cases. Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing consistent and proven advice and instruction for persons on the scene with patients involved with childbirth. This invention, in its best mode of operation, operates as part of a system for the management, processing and response of an emergency medical dispatch system. This emergency medical dispatch system accomplishes the above objectives by: First, gathering necessary medical complaint information from emergency medical inquiry callers and providing emergency verbal instructions to individuals at the scene. Second, prioritizing the complaint to determine the criticality of the emergency. Third, assisting dispatched responders to be prepared for each emergency situation. Fourth, advising those on the way to provide care at the scene of specific problems or potential hazards. When used correctly this invention decreases the effective response time, while increasing the professionalism and control of emergency medical dispatchers, increases the accuracy and appropriateness of patient interrogation and well as the quality of gathered information, reduces the number of multiple unit responses thereby reducing the risk of emergency medical vehicular collisions, improves patient care, reduces burn-out and stress of dispatchers by improving their quality of training, decreases the risk of responder injury or mistake by providing responders with improved knowledge of the situation, provides an means for continuously improving the quality of emergency patient care, and provides a "zero-time" emergency medical response through guidance given remotely, typically over a telephone, to individual at the scene.

While being included within a greater invention that addresses all of the above issues, this invention specifically addresses the method or process of giving emergency medical counsel to childbirth patients and/or those individuals at the scene with the patient. Childbirth is a common yet not routine event. Accurate, reliable and proven instructions can be especially important when childbirth begins or occurs outside a hospital. The process of this invention can be essential to the successful delivery of a new baby, particularly when the travel time for an emergency medical team to the patient is often to long for the team to be able to give the most effective assistance. This invention provides a means for communicating, in an orderly manner, to individuals at the scene the information necessary to help them help with the deliver. Accurate, efficient and systematic responses to calls for help with childbirth can and does make the difference in the successful delivery of many new borns outside the hospital environment.

2. Description of Related Art

It is desirable to provide a systematic and standardized method for responding to emergency medical requests, especially where a woman is about to give birth and where individuals at the scene can be properly instructed help her. Although in the related art some attempt has been made to address the problem of medical care assessment, the related art does not address the specific problems of emergency dispatcher response to medical problems related to childbirth. Rather related art approaches describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein. MICROFICHE APPENDIX. This specification includes a Microfiche Appendix which includes 1 page of microfiche with a total of 20 frames. The microfiche appendix includes computer source code and database structure of one preferred embodiment of the invention. In other embodiments of the invention, the inventive concept may be implemented in other computer code, in computer hardware, in other circuitry, in a combination of these, or otherwise. The Microfiche Appendix is hereby incorporated by reference in its entirety and is considered to be a part of the disclosure of this specification.

SUMMARY OF THE INVENTION

It is desirable to provide a system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation. Furthermore, it is desirable to have an emergency medical dispatch system that includes provisions for instructing, counseling, advising those on the scene in procedures and techniques that can aid a woman in giving birth to a child. It is desirable to have such provisions which incorporate proven techniques for guiding an on-scene individual through the process and which includes a scripted procedure which steps the dispatcher through the process without depending solely on the individual skills and knowledge base of the dispatcher.

Accordingly, it is the primary object of this invention to provide a medical dispatch system that is designed to guide the medical dispatcher through the interrogation, obtaining vital patient information regarding calls concerning women who are about to give birth.

Another object of this invention is to provide a cross-referenced scripted set of instructions to be given by the dispatcher to the caller in a childbirth medical emergency situation.

A further object of this invention is to improve the quality, efficiency and usefulness of the information received to and communicated by emergency medical dispatchers thereby improving the quality of emergency medical services provided to patient before, during and after the arrival of emergency medical technicians.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provides. Each preferred embodiment incorporates the same essential method of this invention, though each has its own particular advantages.

DETAILED DESCRIPTION OF THE INVENTION

This invention provides a method, system and an apparatus for receiving, processing and communicating emergency medical information, specifically related to communicating instructions to individuals at the scene for the emergency assistance of women in the process of childbirth. When the invention is properly employed the initial interrogation of the caller or patient will have previously provided the emergency medical dispatcher critical patient information which has indicated that the patient is most likely about to give birth. This information has been applied in protocols which have led the dispatcher through a scripted interrogation, gathering additional related information, and categorizing the problem by assigning a determinant value establishing the criticality of the problem. This invention then functions by providing appropriate scripted established emergency medical instruction to the individuals on the scene.

Figure 1:
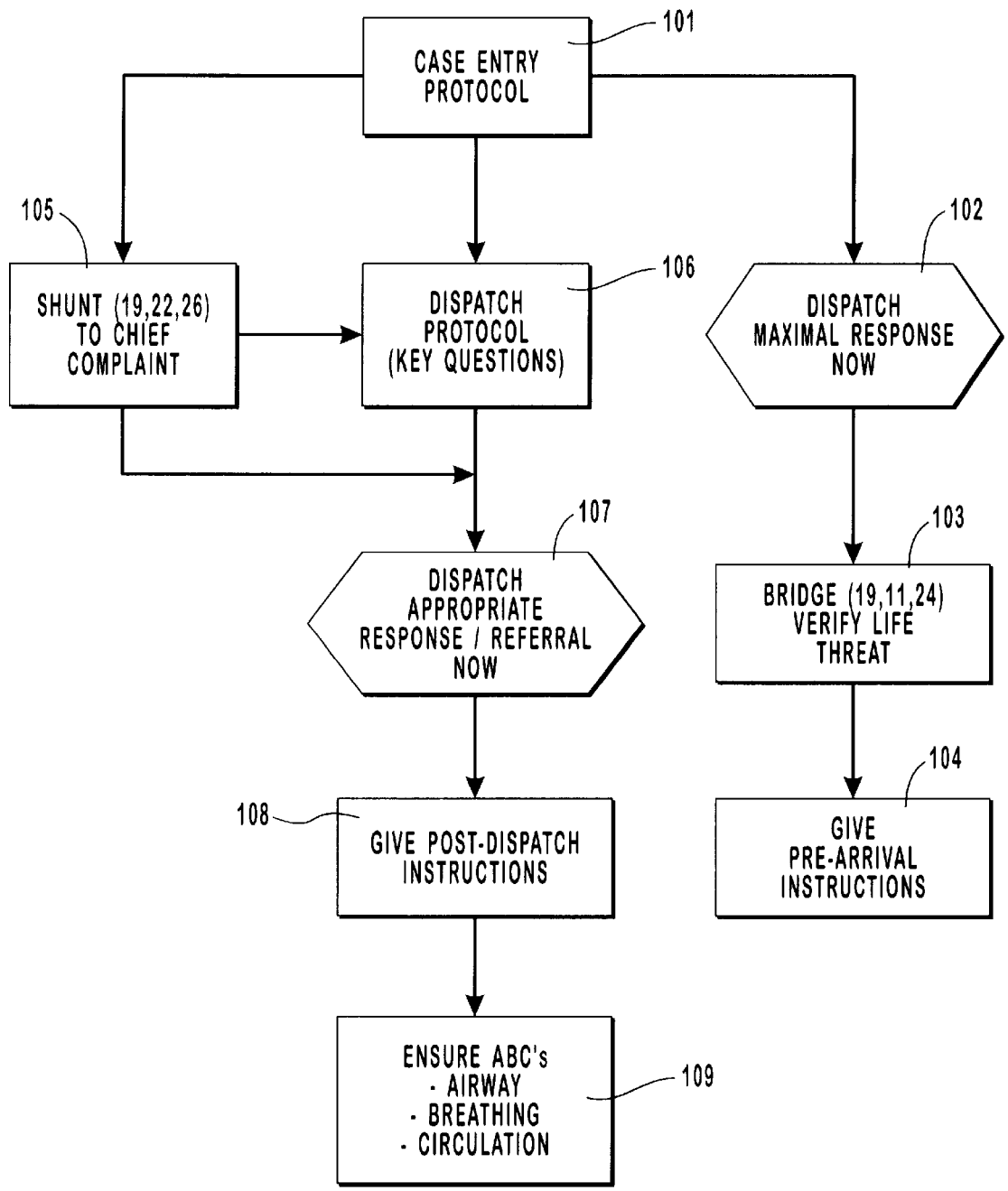
FIG. 1 depicts the principle elements of the complete system in which the preferred embodiment of the invention operates and the relationship of the element, of system to each other, and serves to put this invention in the context of the complete system.

FIG. 1 shows the complete system in which the invention operates in its best mode. The process of managing emergency medical dispatchers, the information they require and the information they give is detailed in FIG. 1. The case entry protocol 101 provides the initial steps through which the all emergency callers or patients are taken to provide symptom information and to access medical information. The purpose of the case entry protocol 101 is to receive sufficient information to permit the dispatcher to identify the caller's chief complaint. This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. A maximum response dispatch 102 may include such resources as emergency medical technicians, ambulances, paramedics, and other appropriate medical care givers. The life threat is then verified 103 and pre-arrival instructions are given 104. These pre-arrival instructions 104 include six treatment sequence scripts covering Arrest, Choking, and Childbirth. The pre-arrival instruction procedure for childbirth is the heart of this invention. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha—A, Bravo—B, Charlie—C, and Delta—D) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section ol the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
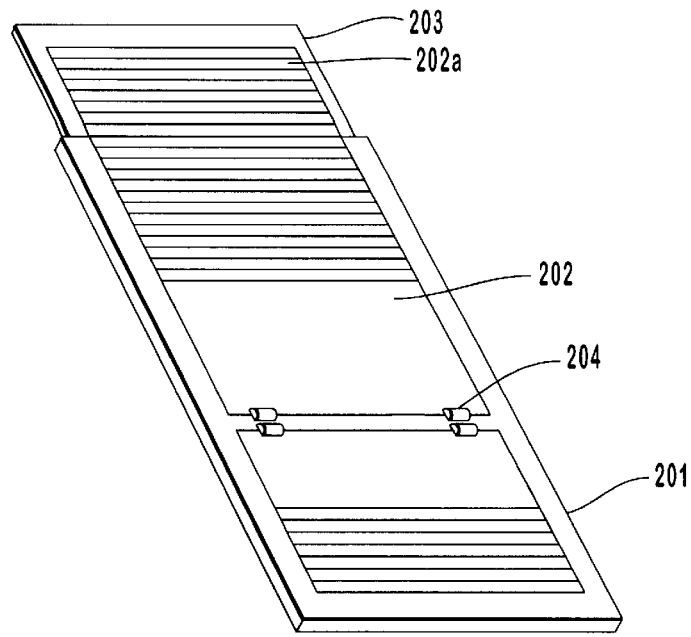
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202a. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
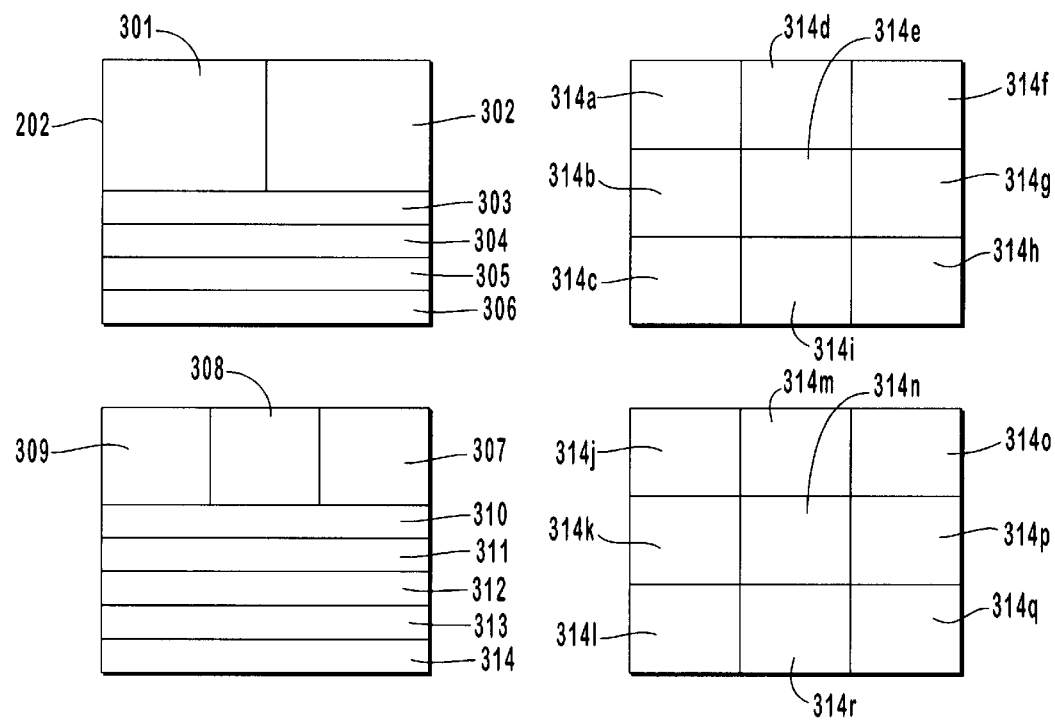
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A-Alpha 303, B-Bravo 304, C-Charlie 305 and D-Delta 306 are provided to aid the dispatcher in making the determinant designation. Each determinant level may have one or more sublevels. Generally, the most critical call is given a determinant level of D-Delta and the least critical call is given a determinant level of A-Alpha. The more critical the determinant level assigned to a call, the more medical resources and urgency may be applied to provide help. For example, an A-Alpha call will typically be responded to by emergency medical technicians and an ambulance proceeding to the patient under the safest method reasonably possible, while a D-Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene and prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314 a–r. These pre-arrival instruction sections 314 provide scripted treatment sequences for arrest, choking and childbirth. These procedures, provided through sections 314, guide the caller through CPR., the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
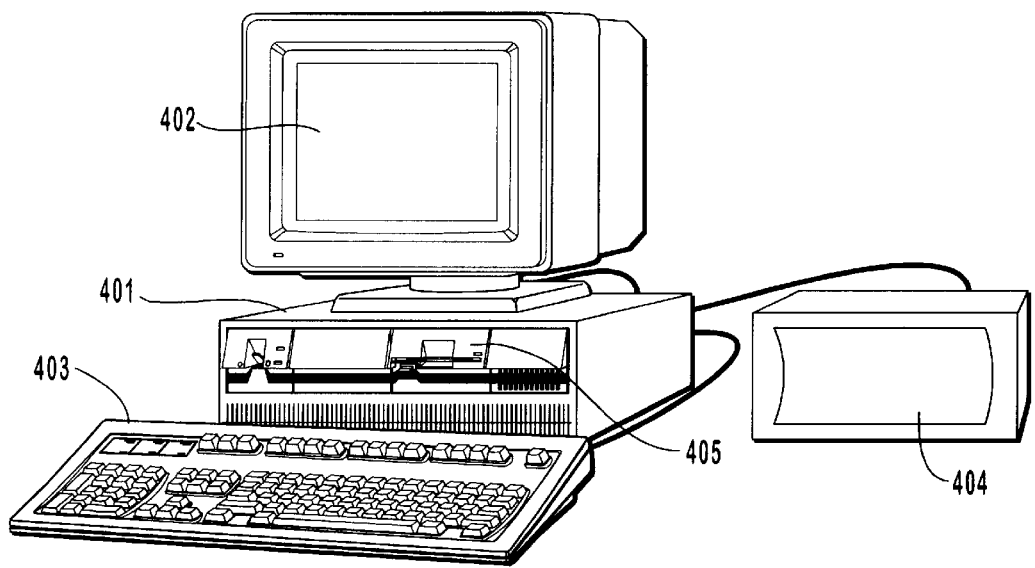
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
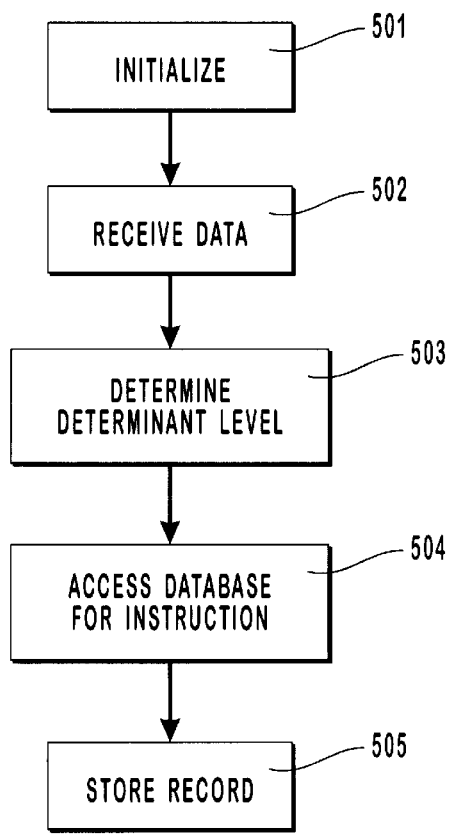
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
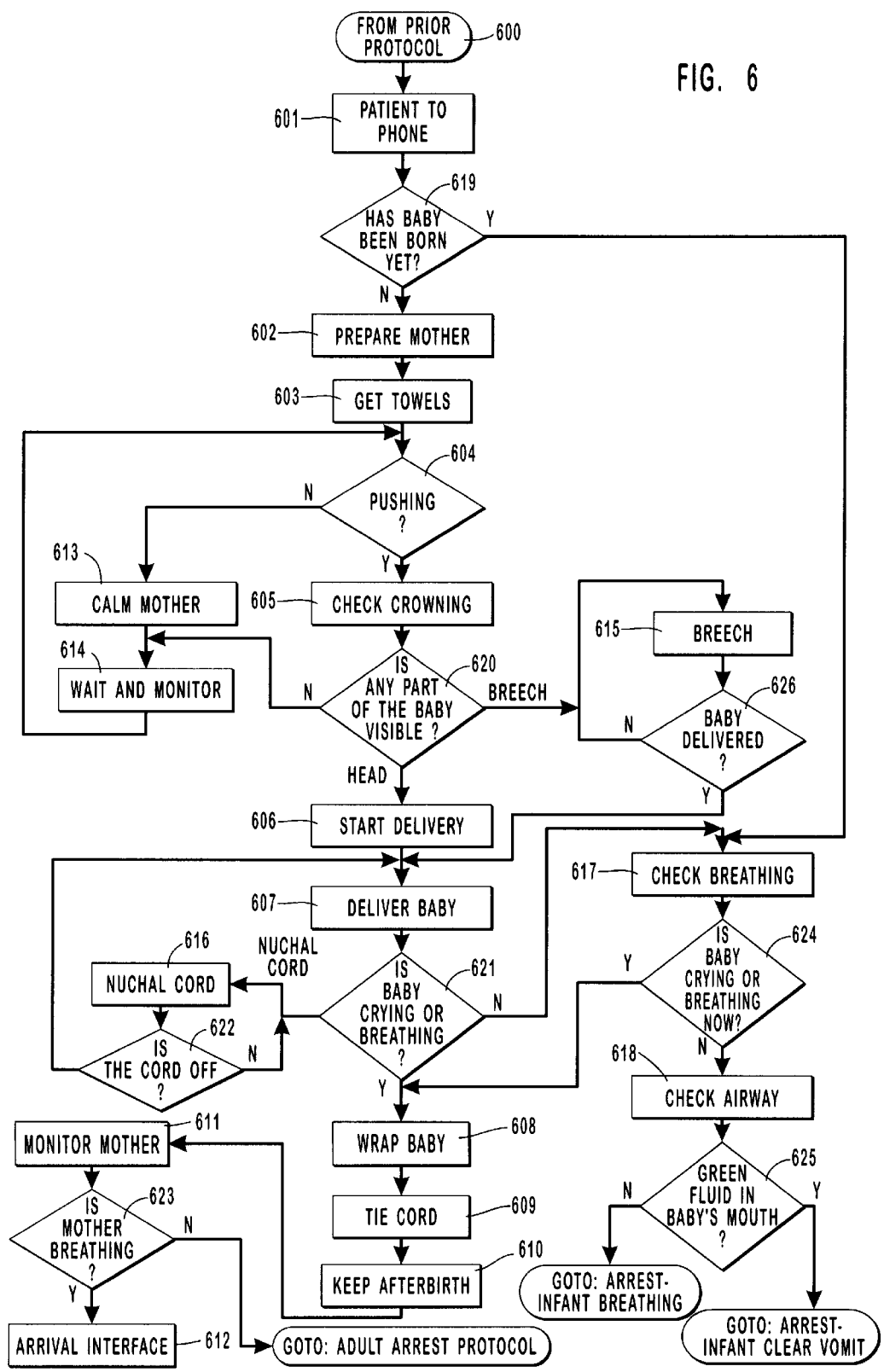
FIG. 6 depicts the detailed steps of the childbirth pre-arrival instructions protocol process, constituting the preferred embodiment of the invention.

FIG. 6 depicts the detailed steps of the childbirth pre-arrival instruction protocol, in a form reflecting the preferred embodiment of the invention. Although the following steps of the protocol process of the invention need not necessarily be accomplished in this specific order, alternative ordering, of the steps of the invention are possible, this order of the steps of the process has been determined by the inventor to be the best mode of the invention. First, this protocol of pre-arrival instructions for childbirth patients is reached, in the best mode of the invention, after the dispatcher has interrogated the caller, determined the type of medical emergency, assigned a determinant value describing the level of emergency and, in general, after the dispatcher has dispatched an emergency medical response team to the site of the arrest emergency. The following procedure of this invention is performed as a systematic means of providing interim emergency medical instruction to individuals at the scene. Therefore, this invention is generally reached from a prior emergency medical protocol 600. After each step the caller is instructed to "Do it now and then come right back to the phone." The caller is instructed to bring the patient as close to the phone as possible 601 and to get the patient on her back in the center of a bed or on the floor. The caller is also told that the dispatcher is going to help deliver the baby. During this step the caller is also asked where the patient is now and if the baby has been born yet 619. If the baby has already been born, the dispatcher jumps to the check breathing step 617 where the breathing of the baby is verified. If the baby has not yet been born, the caller is instructed to prepare the mother for the delivery 602, by making sure that she has removed all clothing below her waist, that her head is raised with pillows, but that she doesn't sit up or go to the bathroom. Next, the caller is instructed to get towels 603 and a blanket to wrap the baby in, as well as a string or shoelace to tie around the umbilical cord after delivery. The caller is next asked wither the patient is pushing or straining with the pains yet 604. If she is not, the caller is instructed to calm the mother 613 by telling her that everything should be fine and to take slow deep breaths between the contractions. The caller then is told to wait and monitor 614 the progress and to let the dispatcher know right away if anything changes.

If the patient is pushing or straining with the pain now, the caller is told to check the crowning 605, that is to look at the patient's vagina to see how close the baby is to being born. The dispatcher then inquires as to whether any part of the baby is coming out yet 620. If the answer is no, then the dispatcher instructs the caller to wait and monitor 614 the patients condition. If, however, some of the baby is visible, then the caller must determine whether the baby is coming normally or breech. A normal delivery involves a baby being born head first. A breech delivery involves a baby being born with some other part of the body first. Breech births carry with them special risks and must be handled carefully. If it appears that a breech birth is likely, the dispatcher goes to the breech step of the process 615. This step involves telling the caller that this could be a very difficult delivery, that the patient should get up on her elbows and knees and should stop pushing the with the pains and should take deep breaths with each contraction. If any more of the baby starts to deliver the dispatcher should be notified immediately, in which case the dispatcher returns to the deliver the baby step 607.

If the head is visible, this means that a normal delivery is expected and the caller is instructed to start the delivery 606, by with each contraction placing the realm of the caller's hand against the patients vagina and applying firm by gentle pressure to keep the baby's head from delivering to fast and tearing the patient. Next, the caller is told to deliver the baby 607. As the head delivers, the baby's mouth and nose should be cleaned with a dry towel. The caller is reminded that the baby will be slippery and to be careful not to drop the baby. After the baby is born the caller should support the baby's head and shoulders and hold the hips and legs firmly. At this point the caller is asked whether the baby is crying or breathing 621, the caller is instructed to gently slap the bottom of the baby's feet and to listen for crying or breathing. If the baby is not crying or breathing now, the caller is instructed to check the baby's airway 618 by placing the caller's hand under the baby's neck and shoulders, slightly tilting the baby's head back and checking if there is any green fluid in its mouth. If there is green fluid in its mouth the dispatcher goes to the Arrest-Infant Protocol to clear the vomit from the baby's mouth. If there is not green fluid in the baby's mouth, the dispatcher goes to the Arrest-Infant Protocol for infant breathing problem procedures.

If the baby is breathing now, the caller is instructed to wrap the baby 608 with a clean towel, and then wrap the baby in a dry towel to keep it warm. Cover the baby's head but not its face. Next, the caller is instructed to tie the cord 609 by tying a string around the umbilical cord approximately six inches from the baby. Do not cut it. Lay the baby on the mother's stomach. Be sure to keep the baby and mother warm. The caller is instructed not to pull on the cord. When the afterbirth is delivered, to wrap it in a towel and to keep it 610. The doctor will need to examine it to make sure it all came out. The caller is then instructed to monitor the mother 611 by making sure the mother is kept warm and to make sure she feels alight. The caller should be sure the mother is breathing 623, if she is not breathing the dispatcher goes to the Adult Arrest Protocol. If the mother is breathing and well, the caller is instructed to wait for the paramedics 612, not to leave the mother alone and to hand the phone to one of the paramedics when they arrive. The caller should be certain that the door is unlocked and should send someone to open it.

Figure 7:
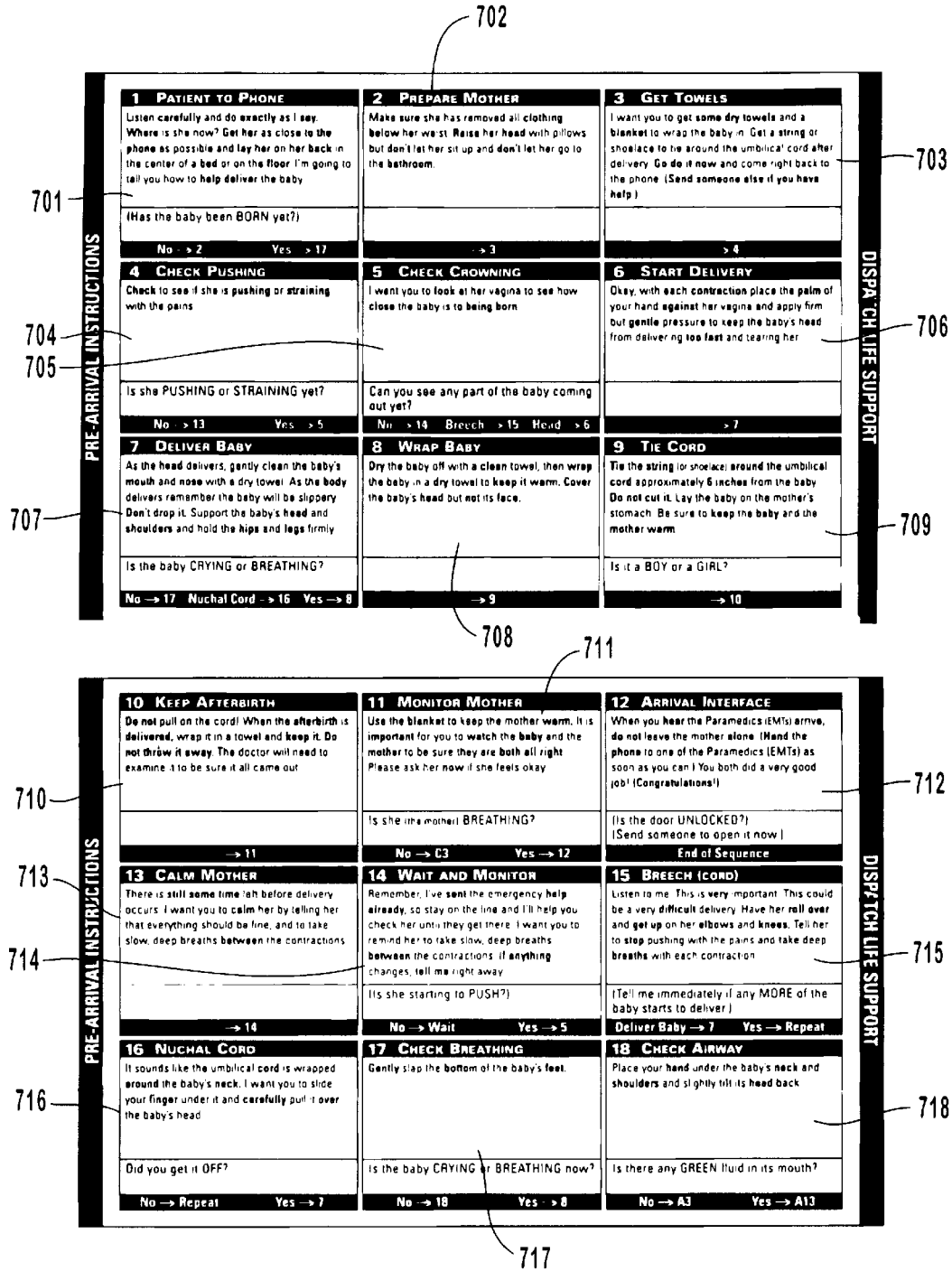
FIG. 7 shows the steps of the choking adult pre-arrival instructions protocol of the flip card deck embodiment of the invention.

FIG. 7 depicts the preferred embodiment of the flip cards showing the steps of the arrest-infant pre-arrival instruction protocol invention. The patient to phone step is shown 701. The prepare mother step is shown 702. The get towels step is shown 703. The check pushing step is shown 704. The check crowning step is shown 705. The start delivery step is shown 706. The deliver baby step is shown 707. The wrap baby step is shown 708. The tie cord step is shown 709. The keep afterbirth step is shown 710. The monitor mother step is shown 711. The arrival interface step is shown 712. The calm mother step is shown 713. The wait and monitor step is shown 714. The breech step is shown 715. The nuchal cord step is shown 616. The check breathing step is shown 617. The check airway step is shown 618.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for giving remote emergency medical counsel to childbirth patients, comprising the steps of:
   (A) receiving a medical call on a telephone communication device regarding a childbirth patient needing medical assistance;
   (B) instructing an emergency medical dispatcher to inquire from said received medical call whether said childbirth patient is pushing, whether crowning has occurred, and whether the baby when delivered is breathing;
   (C) determining whether said childbirth patient is pushing;
   (D) if said childbirth patient is pushing, checking for crowning, wherein said childbirth patient is examined to determine whether a part of a baby is visible;
   (E) determining whether said visible part of said baby is a head, and if said visible part of said baby is a head, starting delivery and delivering said baby and checking if said baby is breathing;
   (F) determining whether said visible part of said baby is not a head, and if said visible part of said baby is not a head, identifying that said baby is coming breech, and holding off delivery if possible, delivering said baby if necessary and checking if said baby is breathing;
   (G) if said childbirth patient is not pushing, calming said childbirth patient and waiting and monitoring;
   (H) calculating a determinate value based on whether said childbirth patient is pushing; said crowning has occurred; and whether said baby is breathing; and
   (I) dispatching medical assistance based on said calculated determinate value to said childbirth patient.

2. A method for managing a process of responding to relate medical injuries relating to childbirth patients, the system comprising:
   (A) a first inquiry, communicated over a telephone communication device, as to whether the childbirth patient is pushing;
   (B) if the patient is pushing, an instruction communicated over said telephone communication device to check for crowning, wherein the childbirth patient is examined to determine whether a part of a baby is visible;
   (C) if said visible part of said baby is a head, an instruction communicated over said telephone communication device instructing to start delivery and delivering said baby and checking if said baby is breathing;
   (D) if said visible part of said baby is not a head, an instruction identifying that said baby is coming breech, holding off delivery if possible, delivering said baby if necessary and checking if said baby is breathing;
   (E) if the patient is not pushing, calming the childbirth patient and waiting and monitoring;
   (F) calculating a determinate value based on whether said childbirth patient is pushing, and whether said baby is coming breech or is coming head first; and
   (G) based upon said determinate dispatching medical assistance to said childbirth patient.

3. A method for managing the process for responding to an emergency medical call relating to a childbirth patient in a general purpose computer system comprising:
   a central processing unit;
   dynamic memory,
   static memory,
   a display device,
   an input device,
   an output device,
   a mass storage device which contains
   a number of emergency medical instruction records,
   a number of medical information records,
   a grouping of determinant codes,
   a number of emergency medical inquiry reports,
   the method comprising the steps of:
   (A) displaying on said display device an instruction for determining by communication over a telephone communication device if the childbirth patient is pushing;
   (B) receiving to said dynamic memory by way of said input device a result of said determination of whether the childbirth patient is pushing;
   (C) if said result of said determination of whether the childbirth patient is pushing indicates that the childbirth patient is pushing, displaying on said display device an instruction to check for crowning, wherein the childbirth patient is examined to determine whether a part of a baby is visible;
   (D) receiving to said dynamic memory by way of said input device a result of said check for crowning;
   (E) if said result of said check for crowning indicates that said visible part of said baby is a head, displaying on said display device an instruction to start delivery and once said baby is delivered displaying an instruction on said display device to check if said baby is breathing and inputting via said input device whether said baby is breathing;
   (F) if said result of said check for crowning indicates that said visible part of said baby is not a head, displaying an instruction on said display device identifying that said baby is coming breech, displaying an instruction on said display device to hold off delivery if possible, and to only deliver said baby if necessary and displaying an instruction on said display device to check if said baby is breathing and inputting via said input device whether said baby is breathing;
   (G) if said result of said determination of whether the childbirth patient is pushing indicates that the childbirth patient is not pushing; displaying on said display device an instruction to calm the childbirth patient and to wait and monitor;
   (H) said processor calculating a determinate value based on said received determination of whether the childbirth patient is pushing, said received check for crowning result and said baby breathing input; and
   (I) based on said determinate value, displaying an instruction for dispatching medical assistance to said childbirth patient.

\* \* \* \* \*